United States Patent
Harkness (10) Patent No.: US 8,439,888 B2
(45) Date of Patent: May 14, 2013

(54) THREE-PIECE DISPOSABLE ABSORBENT ARTICLE HAVING AN ABSORBENT WITH CROSS-DIRECTION FLEXIBILITY

(75) Inventor: Stephen Scott Harkness, Greenville, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1679 days.

(21) Appl. No.: 11/445,364

(22) Filed: Jun. 1, 2006

(65) Prior Publication Data

US 2007/0282292 A1 Dec. 6, 2007

(51) Int. Cl.
*A61F 13/15* (2006.01)

(52) U.S. Cl.
USPC .................................... 604/385.22

(58) Field of Classification Search ............. 604/385.22, 604/385.16
See application file for complete search history.

(56) References Cited

U.S. PATENT DOCUMENTS

| | | | |
|---|---|---|---|
| 4,323,070 A | 4/1982 | Ternstrom et al. | |
| 4,534,769 A | 8/1985 | De Jonckheere et al. | |
| 4,701,172 A | 10/1987 | Stevens | |
| 4,720,415 A | 1/1988 | Vander Wielen et al. | |
| 4,731,066 A | 3/1988 | Korpman | |
| 4,756,709 A | 7/1988 | Stevens | |
| 4,886,511 A | 12/1989 | Korpman | |
| 4,892,598 A | 1/1990 | Stevens et al. | |
| 5,269,775 A | 12/1993 | Freeland et al. | |
| 5,336,545 A | 8/1994 | Morman | |
| 5,366,793 A | 11/1994 | Fitts, Jr. et al. | |
| 5,385,775 A | 1/1995 | Wright | |
| 5,527,303 A | 6/1996 | Milby, Jr. et al. | |
| 6,049,023 A | 4/2000 | Blenke et al. | |
| 6,149,638 A | 11/2000 | Vogt et al. | |
| 6,375,646 B1 | 4/2002 | Widlund et al. | |
| 6,521,811 B1 * | 2/2003 | Lassen et al. ................. | 604/378 |
| 6,702,801 B2 | 3/2004 | Van Gompel et al. | |
| 6,979,380 B2 | 12/2005 | Thorson et al. | |
| 2002/0119722 A1 | 8/2002 | Welch et al. | |
| 2002/0120249 A1* | 8/2002 | Wada et al. .............. | 604/385.24 |
| 2002/0169432 A1 | 11/2002 | Fell et al. | |
| 2004/0060649 A1 | 4/2004 | Van Gompel et al. | |
| 2004/0122401 A1* | 6/2004 | Van Gompel et al. ... | 604/385.14 |
| 2004/0210205 A1 | 10/2004 | Van Gompel et al. | |
| 2005/0107763 A1 | 5/2005 | Matsuda et al. | |
| 2005/0148965 A1 | 7/2005 | Richlen et al. | |

(Continued)

FOREIGN PATENT DOCUMENTS

| | | |
|---|---|---|
| DE | 40 18 097 C1 | 8/1991 |
| EP | 1 661 535 A1 | 5/2006 |
| WO | WO 00/30584 A1 | 6/2000 |
| WO | WO 2004/052260 A1 | 6/2004 |
| WO | WO 2004/108038 A1 | 12/2004 |

*Primary Examiner* — Melanie Hand
(74) *Attorney, Agent, or Firm* — H. Michael Kubicki (57) ABSTRACT

A three-piece disposable absorbent article is disclosed having a longitudinal central axis and a transverse central axis. The disposable absorbent article includes front and back panels, each panel capable of being stretched and retracted in multiple directions. The back panel is also distinct and spaced apart from the front panel. The disposable absorbent article further includes an absorbent assembly situated between the front and back panels and which is attached to each by a first attachment member. The first attachment member is aligned along the longitudinal central axis. The disposable absorbent assembly includes a non-elastic absorbent that is capable of being elongated and contracted in only one direction, that direction being aligned approximately parallel to the transverse central axis.

13 Claims, 3 Drawing Sheets

U.S. PATENT DOCUMENTS

| | | |
|---|---|---|
| 2005/0177124 A1 | 8/2005 | Kondo |
| 2005/0256489 A1 | 11/2005 | Sawyer et al. |
| 2006/0004341 A1 | 1/2006 | Olson et al. |
| 2006/0004342 A1 | 1/2006 | Sawyer et al. |

* cited by examiner

THREE-PIECE DISPOSABLE ABSORBENT ARTICLE HAVING AN ABSORBENT WITH CROSS-DIRECTION FLEXIBILITY

BACKGROUND OF THE INVENTION

Disposable absorbent articles are available in many different sizes, styles and configurations and are designed for absorbing human exudate, such as urine and fecal matter. Such disposable absorbent articles are intended to be worn by infants, toddlers and adults and are designed for single use. By "single use" it is meant that the disposable absorbent article will be disposed of after being used once instead of being laundered or cleaned for reuse, as is typical of cloth underwear. Examples of some disposable absorbent articles include an infant diaper, a child training pant, a feminine menstrual pant and an adult incontinent undergarment. Many of such disposable absorbent articles are similar in appearance, size and shape as regular cloth underwear except that they are formed from a variety of materials, including absorbent and elastic materials. The absorbent materials allow the disposable absorbent article to absorb and retain body waste while the elastic materials permit the disposable absorbent article to closely conform to the anatomy of the user's torso.

Most manufacturers of such disposable absorbent articles are constantly looking to improve the appearance and normalcy of such articles to simulate cloth underwear. One important functional element is fit. The disposable absorbent article must fit comfortably against the wearer's body while preventing fluid leakage. It has been discovered that constructing a disposable absorbent article using three separate and distinct panels, instead of a single panel, allows for greater flexibility and better fit. In addition, the use of new elastic materials, which have the ability to stretch and retract in more than one direction, have allowed manufacturers to construct disposable absorbent articles that conform more closely to the wearer's torso. This is especially noticeable around the waist and leg openings and the areas overlaying the stomach and buttock regions. However, the crotch portion of many disposable absorbent articles still needs to be improved. The crotch portion needs to have resiliency mainly in the transverse or cross-body direction in order to elongate and rebound from movement of the wearer's thighs. As a wearer walks, his or her thighs move forward relative to each other and this causes the crotch portion to rope and twist. In addition, when the wearer moves his or her thighs closer together, the crotch portion will be subjected to compressive forces. Likewise, when the wearer moves his or her thighs apart, the crotch portion will need to quickly move back towards its original size and dimension. This need for the absorbent to elongate and contract in the transverse or cross-body direction is desirable in preventing fluid leakage.

Now a three-piece, disposable absorbent article has been invented that has an absorbent assembly that includes a non-elastic absorbent that is capable of being elongated and contracted in the transverse or cross-body direction as the backsheet is stretched and retracted.

SUMMARY OF THE INVENTION

Briefly, this invention relates to a three-piece disposable absorbent article having a longitudinal central axis and a transverse central axis. The disposable absorbent article includes front and back panels, each panel capable of being stretched and retracted in multiple directions. The back panel is also distinct and spaced apart from the front panel. The absorbent article further includes an absorbent assembly situated between the front and back panels. The disposable absorbent assembly is attached to the front and back panels by a first attachment member. The first attachment member is aligned along the longitudinal central axis. The disposable absorbent assembly includes a liquid permeable, elastic bodyside liner, a liquid-impermeable, elastic backsheet and a non-elastic absorbent positioned therebetween. The non-elastic absorbent is capable of being elongated and contracted approximately in the transverse or cross-body direction as the backsheet is stretched and retracted.

DETAILED DESCRIPTION

Figure 1:
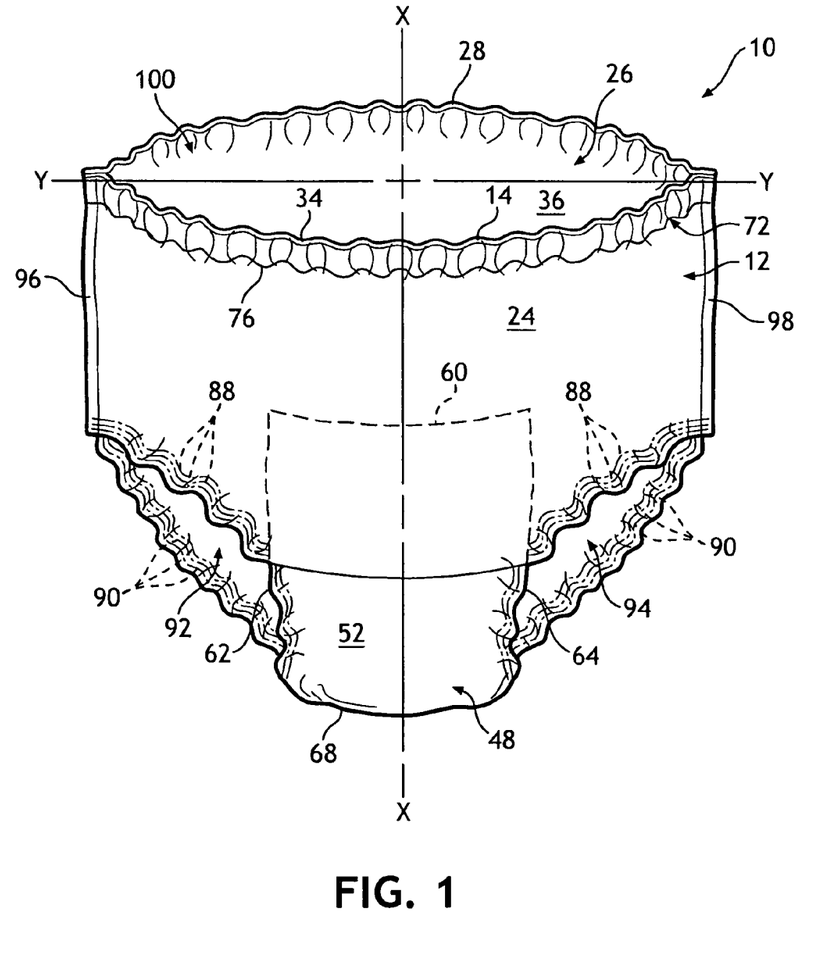
FIG. 1 is a perspective view of a three-piece disposable absorbent article having an absorbent with cross-direction flexibility.

Referring to FIG. 1, a three-piece disposable absorbent article 10 is depicted that is designed for absorbing human exudate, such as urine and fecal matter. The three-piece disposable absorbent article 10 is intended to be worn by toddlers or adults who have the ability to step into the product. The three-piece disposable absorbent article 10 is designed for a single use and is meant to be disposed of after being used once instead of being laundered or cleaned for re-use. The three-piece disposable absorbent article 10 is designed to be pulled up around the user's torso without having to first open the absorbent article 10 in order to place it on a person's body. In FIG. 1, the three-piece disposable absorbent article 10 is shown as an adult incontinent undergarment. The three-piece disposable absorbent article 10 is shown having its normal appearance after it has been removed from its packaging and just prior to being pulled up along a user's legs and adjusted about the user's torso.

Figure 2:
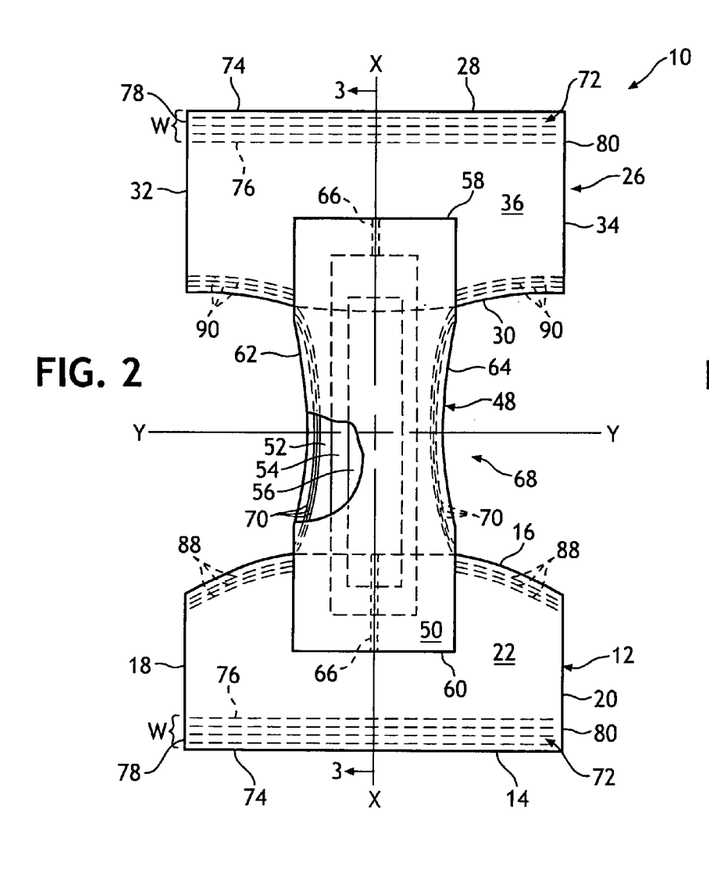
FIG. 2 is a plane view of the three-piece disposable absorbent article shown in FIG. 1 but depicted in an open position so as to reveal the absorbent assembly being secured to the inner surfaces of the front and back panels and showing a partial cut away view of the construction of the absorbent assembly.
Figure 3:
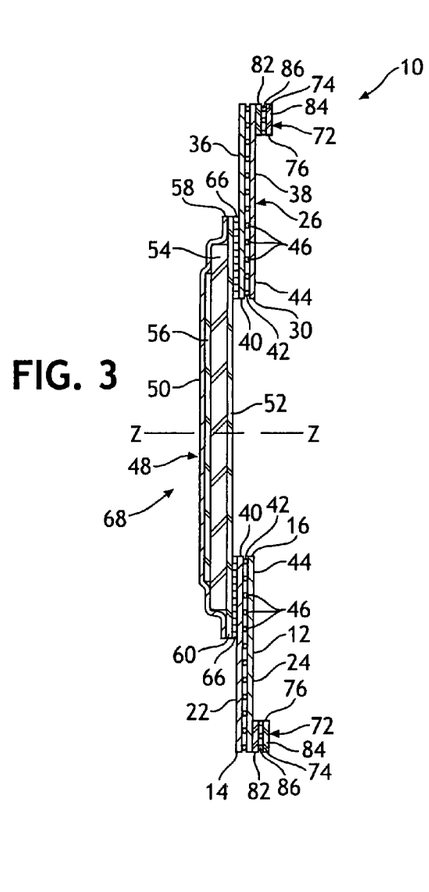
FIG. 3 is a cross-section view of the three-piece disposable absorbent article shown in FIG. 2 taken along line 3-3.

Referring to FIGS. 2 and 3, the three-piece disposable absorbent article 10 is depicted in an open configuration solely for the purpose of better showing the various components. The three-piece disposable absorbent article 10 has a longitudinal central axis X-X, a transverse central axis Y-Y and a vertical central axis Z-Z. The three-piece disposable absorbent article 10 includes a front panel 12 having a first end 14 spaced apart from a second end 16 and a first side edge 18 spaced apart from a second side edge 20. Desirably, the first end 14 is linear although it could have a scalloped, serpentine or non-linear configuration, if desired. The front panel 12 has an interior surface 22 and an exterior surface 24. The interior surface 22 faces and contacts the body of the user when the three-piece disposable absorbent article 10 is worn.

The exterior surface 24 is aligned opposite to the interior surface 22 and faces away from the body of the user when the disposable absorbent article 10 is worn.

The front panel 12 is formed from an elastic material that is capable of being stretched and retracted in multiple directions. By "stretched" it is meant that the front panel 12 can be lengthened, widened, extended or increased in dimension by applying a force, such as by pulling. By "retracted" it is meant that the front panel 12 can be shortened, decreased or reduced in dimension or returned to or towards its original size after the force used to stretch the front panel 12 has been removed. Desirably, the front panel 12 will quickly retract or return to its original pre-stretched length once the force used to stretch the front panel 12 has been removed. For example, a 1 inch (2.54 cm) strip of material can be stretched to about 2 inches (about 5 cm) and then when the stretching force is removed, the material will retract to or towards its original pre-stretched length of 1 inch (2.54 cm). The original width of the front panel 12 is measured as the distance between the first and second side edges, 18 and 20 respectively. The retracted dimension is measured after the force required to stretch the material has been removed. By "multiple directions" it is meant that the front panel 12 can be stretched and retracted in at least three different directions. Desirably, the front panel 12 can be stretched and retracted in more than three directions.

The front panel 12 is formed from an elastic material that is stretchable and retractable in multiple directions. By "elastic" it is meant that the material is capable of being stretched when a tensile force is applied and the material can retract quickly or immediately to or towards its original dimension(s) once the force is removed. Examples of stretchable materials include natural and synthetic rubbers, elastic films, elastic filaments, elastic threads, elastic strands, laminates formed from two or more layers wherein at least one of the layers is elastic, etc. For example, a laminate formed from an elastic film sandwiched between two or more non-elastic layers. The front panel 12 can also be formed from an elastic net-like material or a material formed from a plurality of elastic strands aligned in two different planes. When a plurality of elastic strands is utilized, they can be positioned on a single carrier layer or be positioned between two or more layers. Other elastic materials that can be used include spunbond, a spunbond laminate, a neck bonded laminate, as well as other material known to those skilled in the art. Spunbond is a material manufactured and commercially sold by Kimberly-Clark Corporation, having an office at 401 North Lake Street, Neenah, Wis. 54956. Examples of some stretchable materials and/or the process for making such stretchable materials are taught and described in U.S. Pat. Nos. 4,720,415; 5,336,545; 5,366,793; 5,385,775 and in Patent Publication 2002/0119722A1 dated Aug. 29, 2002, all of which are incorporated by reference and made a part hereof.

The three-piece disposable absorbent article 10 also includes a back panel 26 having a first end 28 spaced apart from a second end 30 and a first side edge 32 spaced apart from a second side edge 34. Desirably, the first end 28 is linear although it could have a scalloped, serpentine or non-linear configuration, if desired. The back panel 26 is elastic and has an interior surface 36 and an exterior surface 38. The interior surface 36 faces and contacts the body of the user when the three-piece disposable absorbent article 10 is worn. The exterior surface 38 is aligned opposite to the interior surface 36 and faces away from the body of the user when the disposable absorbent article 10 is worn.

The same definitions recited above for the words "stretched, retracted, multiple directions and elastic" also apply to the back panel 26. The original width of the back panel 26 is the distance between the first and second side edges, 32 and 34 respectively. The retracted dimension is measured after the force required to stretch the material has been removed.

The front and back panels, 12 and 26 respectively, are distinct members. By "distinct" it is meant that the front and back panels, 12 and 26 respectively, are separate and easily distinguishable from all other members. The front and back panels, 12 and 26 respectively, are spaced apart from one another and are discontinuous from one another along the longitudinal central axis X-X. For example, the front panel 12 can be spaced at least about 3 inches (about 76 mm) or more from the back panel 26.

The interior surfaces 22 and 36 of the front and back panels, 12 and 26 respectively, are in direct contact with the user's skin when the three-piece disposable absorbent article 10 is being worn and are sometimes referred to as the bodyside surfaces. The exterior surfaces 24 and 38 are situated opposite to the interior surfaces 22 and 36 and are spaced away from the user's skin. The exterior surfaces 24 and 38 are sometimes referred to as the garment facing surfaces since they can be in direct contact with the inner surfaces of the user's outer clothing.

Each of the front and back panels, 12 and 26 respectively, is formed such that essentially the entire panel 12 and 26 is capable of being stretched and is also capable of being retracted. By "essentially the entire" it is meant that approximately between about 90% to 100% of the front panel 12 is stretchable and retractable and approximately between about 90% to 100% of the back panel 26 is stretchable and retractable.

Referring now to FIG. 3, each of the front and back panels, 12 and 26 respectively, is shown being formed as a three-layer laminate. Each of the front and back panels, 12 and 26 respectively, includes a first layer 40, a second layer 42, and a third layer 44. The first and third layers, 40 and 44 respectively, are the outer layers and can be formed from the same material or from different materials. The first and third layers, 40 and 44 respectively, can be constructed from natural or synthetic fibers and can be a woven or non-woven material. The second or middle layer 42 has the elastic properties and is sandwiched between the first and third layers, 40 and 44 respectively. It should be noted that one or both of the outer layers 40 or 44 can be made from an elastic material and the second or middle layer can be made from a non-elastic material, if desired. Alternatively, the first, second and third layers can all be formed from an elastic material. The front and back panels, 12 and 26 respectively, can also be formed as a two-layer laminate with at least one of the layers being elastic, if desired.

The elastic laminate needs to provide stretch and retraction in at least three directions. Desirably, the stretch and retraction will be in more than three directions. Even more desirably, the stretch and retraction of the front and back panels, 12 and 26 respectively, are in directions approximately parallel to the X-X and Y-Y axes and directions at an angle to these two axes. It should be noted that when the three-piece disposable absorbent article 10 is worn, the transverse central axis Y-Y will extend laterally across the torso from the left hip to the right hip. Most desirably, the stretch and retraction of the front and back panels, 12 and 26 respectively, are in multiple directions, or stated another way, in three or more directions extending over an arc of 360 degrees. The ability of the front and back panels, 12 and 26 respectively, to stretch and retract will provide a confining force during use of the three-piece disposable absorbent article 10 to ensure that it comfortably conforms to the anatomy of the wearer's torso.

Desirably, the front and back panels, 12 and 26 respectively, are constructed from a stretch bonded laminate (SBL). Exemplary SBL materials are described in U.S. Pat. No. 4,720,415, which is hereby incorporated by reference and made a part hereof. In the stretch bonded laminate, the elastic core or middle layer 42 is elongated before the two outer nonwoven layers 40 and 44 are attached. The attachment can be by an adhesive, by heat, by pressure, by a combination of heat and pressure, etc. Another material option for the front and back panels, 12 and 26 respectively, is a necked bonded laminate (NBL). The NBL material is also a three layer laminate but the elastic core or middle layer 42 is not pre-stretched prior to being attached to the two outer nonwoven layers 40 and 44. The outer layers 40 and 44 are necked stretched before the elastic core or middle layer 42 is attached to them. Exemplary NBL materials are described in U.S. Pat. No. 5,336,545, which is hereby incorporated by reference and made a part hereof. Other examples of elastomeric materials that can be used for the front and back panels, 12 and 26 respectively, include but are not limited to a continuous filament stretch bonded laminate (CFSBL) described in U.S. Pat. No. 5,385,775, a vertical filament laminate (VFL) described in Patent Publication 2002/0119722 A1 dated Aug. 29, 2002, a necked stretch bonded laminate (NSBL) and a necked thermal laminate (NTL). Combinations of the above materials can also be used.

It should also be noted that the front and back panels, 12 and 26 respectively, can be constructed from an elastic film that is capable of being stretched in at least three directions. Alternatively, the front and back panels, 12 and 26 respectively, can be formed from an elastic nonwoven that has multiple directions of stretch and retraction. Extensible materials can also be used to form the front and back panels, 12 and 26 respectively, of the three-piece disposable absorbent article 10. Various other stretchable and elastic materials can also be used which are known to those skilled in the art.

Still referring to FIG. 3, the front and back panels, 12 and 26 respectively, can alternatively be formed from two outer layers 40 and 44 with a plurality of elastic strands 46 sandwiched therebetween. The elastic strands 46 can be formed from LYCRA. LYCRA is a registered trademark of E. I. Du Pont De Nemours & Co., having an office at 1007 Market Street, Wilmington, Del. 19898. The elastic strands 46 can be aligned approximately parallel to one another or be angled or skewed relative to one another. The elastic strands 46 can also be uniformly or randomly spaced apart from one another. The elastic strands 46 can vary in shape, size, configuration, and/or length. The diameter and/or cross-sectional configuration of the elastic strands 46, the decitex (weight in grams per 10,000 meters of a strand) of the elastic strands 46, and the tension imparted into the elastic strands 46 can all be varied to suit one's particular product needs. The elastic strands 46 can have a round, semi-circular, square, rectangular, oval or some other geometrical configuration. The elastic strands 46 can overlap, intersect or crisscross at least one other elastic strand 46. The various ways of positioning, orienting, and adhering the elastic strands 46 to the two outer layers 40 and 44 are well known to those skilled in the art.

Referring again to FIGS. 1-3, the disposable absorbent article 10 also includes an absorbent assembly 48 which is secured to the interior surfaces 22 and 36 of the front and back panels, 12 and 26 respectively. The absorbent assembly 48 includes a liquid permeable bodyside liner 50, a liquid-impermeable backsheet or outer sheet 52, and a non-elastic absorbent 54 positioned therebetween. The bodyside liner 50 and the backsheet 52 are formed from an elastic material. The elastic material is capable of being stretched and retracted in at least one direction, with that direction being approximately parallel to the transverse central axis Y-Y. Desirably, the bodyside liner 50 and the backsheet 52 are capable of being stretched and retracted in at least two directions, with one of those directions being approximately parallel to the transverse central axis Y-Y and the other direction being approximately parallel to the longitudinal central axis X-X. Even more desirably, the bodyside liner 50 and the backsheet 52 are capable of being stretched and retracted in three or more directions, with one of those directions being approximately parallel to the transverse central axis Y-Y and a second direction being approximately parallel to the longitudinal central axis X-X. The absorbent 54, by contrast, is non-elastic. By "non-elastic" it is meant that the absorbent 54 is formed from a material that can not stretch or retract an appreciable amount. By "an appreciable amount" it is meant that the material that can be stretched and retracted more than 10% from its original dimension in a given direction.

The absorbent 54 can be formed from natural or synthetic materials. The absorbent 54 can be made from cellulosic fibers, wood pulp, textile fibers or other absorbent materials known to those skilled in the art. A superabsorbent, in solid form and in the shape of small particles, granules, flakes, etc., can be mixed in with the absorbent material to increase the absorbent capacity of the absorbent 54. The absorbent 54 is non-elastic but because of its unique configuration, it does have the ability to elongate and contract back towards its original dimension. By "elongate" it is meant that the absorbent 54 can be lengthened or extended in a particular direction. By "contract" it is meant that the absorbent 54 can be reduced in size or shortened in a particular direction after it has been elongated. More information about the shape and configuration of the absorbent 54 will be discussed later.

The absorbent assembly 48 can optionally include a surge layer 56 located between the bodyside liner 50 and the absorbent 54. The surge layer 56 can function to rapidly acquire and temporarily retain body fluid, such as urine, before it can be absorbed into the absorbent 54. Desirably, the surge layer 56 is also capable of wicking body fluid lengthwise and/or widthwise across its surface as well as directing the body fluid downward in a z-direction, toward the absorbent 54.

The bodyside liner 50 and the backsheet 52 are secured together to completely enclose the non-elastic absorbent 54. Desirably, the bodyside liner 50 and the backsheet 52 are secured together about their perimeters by an adhesive.

Referring to FIGS. 2 and 3, the absorbent assembly 48 has a first end 58, a second end 60, a first side edge 62 and a second side edge 64. The absorbent assembly 48 is shown secured to the interior surfaces 22 and 36 of the front and back panels, 12 and 26 respectively, by a first attachment member 66. The first attachment member 66 is aligned along the longitudinal central axis X-X of the three-piece disposable absorbent article 10. The first attachment member 66 can be a line of adhesive. The first attachment member 66 can be a continuous line of adhesive or it can be an intermittent line of adhesive. When the first attachment member 66 is a line of adhesive, it will allow the backsheet 52 to stretch and retract as the front and back panels, 12 and 26 respectively, stretch and retract approximate the transverse central axis Y-Y. By "approximately in the transverse central axis Y-Y" it is meant within 30 degrees on each side of the transverse central axis Y-Y. Alternatively, the first attachment member 66 can be a narrow strip of adhesive aligned approximately along the longitudinal central axis X-X. It is also possible to secure the absorbent assembly 48 to the exterior surfaces 24 and 38 of the front and back panels, 12 and 26 respectively, if desired.

The absorbent assembly 48 can be secured to either the interior surfaces 22 and 36 or to the exterior surfaces 24 and 38 of the front and back panels, 12 and 26 respectively, after each panel 12 and 26 has been stretched a predetermined amount. The amount the front and back panels, 12 and 26 respectively, are stretched before the absorbent assembly 48 is attached can vary. One advantage of attaching the absorbent assembly 48 to the interior surfaces 22 and 36 of the front and back panels, 12 and 26 respectively, is that the absorbent assembly 48 will be in direct contact with the wearer's body. This design is beneficial for absorbing body fluids discharged by the wearer and thereby is better at preventing fluid leakage.

The first attachment member 66 can include permanent attachments as well as removable or releasable attachments. Desirably, the first attachment member 66 is a permanent attachment where it is not designed to be removed without destroying the bond. The first attachment member 66 can be formed by using glue, adhesive, ultrasonic bonds, thermal bonds, heat bonds, pressure bonds, heat and pressure bonds, or any other attachment mechanism known to those skilled in the art. The first attachment member 66 can also include a mechanical fastener, such as by sewing with thread, using buttons and button holes, using snaps, by employing hook and loop fasteners, etc. A hook and loop fastener is generally considered a releasable attachment. One type of hook and loop fastener is VELCRO wherein a hook material is releasably engaged into a loop material. VELCRO is a registered trademark of Velcro USA, Inc., having an office at 406 Brown Avenue, Manchester, N.H. 03103.

Alternatively, the first attachment member 66 can be formed over a surface area having a predetermined length and width. The first attachment member 66 can consist of intermittent point bonds that are spaced apart from one another. For example, the intermittent point bonds can be formed by using a hot or a cold melt adhesive or by forming ultrasonic bonds. Various bond formations can be used which are known to those skilled in the art. Desirably, the first attachment member 66 is formed using intermittent bonds because it allows the elastic material forming the front and back panels, 12 and 26 respectively, to gather the absorbent assembly 48 as the elastic contracts. This gathering feature causes the absorbent assembly 48 to remain in direct contact with the user's body prior to and during the time period that the absorbent assembly 48 is being insulted with body fluid.

The front and back panels, 12 and 26 respectively, can be stretched in a direction approximately parallel to the transverse axis Y-Y, or in any other direction or directions, before the absorbent assembly 48 is secured to it. The amount of stretch can vary. No stretch is required if one does not wish to do so. Desirably, the front and back panels, 12 and 26 respectively, are stretched at least about 5% from a relaxed state before the absorbent assembly 48 is secured thereto. Desirably, the front and back panels, 12 and 26 respectively, are stretched at least about 10% from a relaxed state before the absorbent assembly 48 is secured thereto. More desirably, the front and back panels, 12 and 26 respectively, are stretched at least about 25% from a relaxed state before the absorbent assembly 48 is secured thereto. Most desirably, the front and back panels, 12 and 26 respectively, are stretched from between about 25% to about 500% from a relaxed state before the absorbent assembly 48 is secured thereto. The front and back panels, 12 and 26 respectively, extend laterally, along the transverse central axis Y-Y, beyond the first and second side edges, 62 and 64 respectively, of the absorbent assembly 48. The front and back panels, 12 and 26 respectively, also extend longitudinally, along the longitudinal central axis X-X, beyond the first and second ends, 58 and 60 respectively, of the absorbent assembly 48. The size and location of the front and back panels, 12 and 26 respectively, allow the three-piece disposable absorbent article 10 to better conform to the torso of the wearer.

Still referring to FIG. 2, when the absorbent assembly 48 is secured to the front and back panels, 12 and 26 respectively, a crotch panel 68 is formed. The crotch panel 68 separates the front panel 12 from the back panel 26 and is designed to cover the perineum area of the wearer. The crotch panel 68 can cover a distance of a few inches in a child training pant to several inches in an adult incontinence garment. For example, a crotch panel 68 in a child training pant may range from about 2 inches (about 5 centimeters (cm)) to about 10 inches (about 25 cm); while in an adult incontinence garment, the crotch panel 68 may range from about 6 inches (about 15 cm) to about 20 inches (about 51 cm).

The bodyside liner 50 and the backsheet 52 are stretchable and retractable in relation to the front and back panels, 12 and 26 respectively. By constructing the bodyside liner 50 and the backsheet 52 to be stretchable and retractable in relation to the front and back panels, 12 and 26 respectively, it means that the three-piece disposable absorbent article 10 will be more suitably adapted to conform to the wearer's torso as he or she moves about. The reason for this is that the front, back and crotch panels 12, 26 and 68, will all be elastically stretchable and retractable and therefore can stretch and retract to snugly conform to the user's anatomy, especially to the wearer's torso. It is not necessary that the bodyside liner 50 and the backsheet 52 stretch and retract to the same extent as the front and back panels, 12 and 26 respectively. However, it is desirable if they do.

It should be noted that there is no need to have the absorbent assembly 48 gather as the front and back panels, 12 and 26 respectively, retract. However, if one so desires, the absorbent assembly 48 can be constructed and attached to the front and back panels, 12 and 26 respectively, in a way that will allow the absorbent assembly 48 to be gathered as the front and back panels, 12 and 26 respectively, elastically retract in a direction approximately parallel to the transverse central axis Y-Y.

The absorbent assembly 48 should remain over the perineum. As the absorbent assembly 48 receives body fluid and/or excrement discharged by the wearer, the middle section of the absorbent assembly 48, which is situated adjacent to the transverse central axis Y-Y, will be displaced outward, away from the user's torso. The first attachment 66 will assure that the absorbent assembly 48 will be aligned over the perineum of the user while allowing the absorbent assembly 48 to move outward, in the z-direction, away from the torso as additional body fluid is received and retained.

Still referring to FIGS. 2 and 3, the absorbent assembly 48 also has at least one elastic member 70 positioned adjacent to and aligned approximately parallel to each of its first and second side edges 62 and 64. Each of the elastic members 70 is situated between the bodyside liner 50 and the backsheet 52. Each of the elastic members 70 provides a gasket to hold the side edges 62 and 64 of the absorbent assembly 48 against the user's body. Each of the elastic members 70 can be in the form of an elastic strand, ribbon or strip. Desirably, there are from about 2 to about 6 elastic members 70 positioned adjacent to each of the side edges 62 and 64. In FIGS. 2 and 3, three elastic members 70 are shown positioned adjacent to each of the side edges 62 and 64. The elastic members 70 can have a cross-sectional configuration that is round, square, rectangular or any other desired geometrical configuration. The elastic members 70 can be aligned parallel or at an angle to the longitudinal central axis X-X and should extend completely through the crotch panel 68. Desirably, the elastic members 70 have an arcuate profile. The opposite ends of the elastic members 70 can terminate short of the front and back panels, 12 and 26 respectively, as shown in FIG. 2 or they can extend into the front and back panels, 12 and 26 respectively, if desired.

Still referring again to FIGS. 2 and 3, the three-piece disposable absorbent article 10 also includes a waist band 72 formed from an elastic material. The waist band 72 is shown being secured to the exterior surfaces 24 and 38 of the front and back panels, 12 and 26 respectively. The waist band 72 can be attached in a non-stretched or semi-stretched condition. By "semi-stretched" it is meant that the waist band 72 is not stretched to stop or fully stretched. The waist band 72 can be secured to the front and back panels, 12 and 26 respectively, by using ultrasonics, by a thermal bond, by adhesive, by heat, by pressure, by a combination of heat and pressure, or a combination of any of the above. The waist band 72 can also be secured to the front and back panels, 12 and 26 respectively, by a mechanical attachment, such as by sewing with thread. Other means of securing the waist band 72 to the front and back panels, 12 and 26 respectively, which are known to those skilled in the art, can also be used.

The waist band 72 has a first end 74, a second end 76, a first side edge 78 and a second side edge 80. As shown in FIGS. 1-3, the first end 74 is coterminous with the first ends 14 and 28 of the front and panels, 12 and 26 respectively. The first end 74 can be spaced apart from the first ends 14 and 28, if desired.

Referring again to FIG. 2, the first and second side edges, 78 and 80 respectively, of the waist band 72 are aligned with the first and second side edges, 18 and 20 respectively, of the front panel 12 and also with the first and second side edges, 32 and 34 respectively, of the back panel 26. The waist band 72 has a width, denoted as (w), which can range from between about 3 millimeters (mm) to about 150 mm. Desirably, the width (w) of the waist band 72 will range from between about 5 mm to about 100 mm. More desirably, the width (w) of the waist band 72 will range from between about 10 mm to about 50 mm. Most desirably, the width (w) of the waist band 72 will range from between about 12 mm to about 25 mm.

Referring again to FIGS. 2 and 3, the waist band 72 can be constructed as a laminate consisting of two outer layers 82 and 84 having one or more elastic strands 86 secured therebetween. Desirably, multiple elastic strands 86 will be positioned between the two outer layers 82 and 84. The two outer layers 82 and 84 can be formed from a non-elastic material. The non-elastic material can be various woven or non-woven materials. An example of a non-woven material that can be used to form one or both of the two outer layers 82 and 84 is polypropylene spunbond. The elastic strands 86 can be formed from LYCRA. At least one of the elastic strands 86 in the waist band 72 can extend from the first side edge 78 to the second side edge 80. Desirably, all of the elastic strands 86 in the waist band 72 will extend from the first side edge 78 to the second side edge 80, as is depicted in FIG. 2. Alternatively, one or more of the elastic strands 86 in the waist band 72 will not extend from the first side edge 78 to the second side edge 80. For example, one or more of the elastic strands 86 in the waist band 72 can extend over only a portion of the distance located between the first and second side edges, 78 and 80 respectively.

The elastic strands 86 can be aligned approximately parallel to one another or be angled or skewed relative to one another. The elastic strands 86 can also be uniformly or randomly spaced apart from one another. The elastic strands 86 can vary in shape, size, configuration, and/or length. The diameter and/or cross-sectional configuration of the elastic strands 86, the decitex (weight in grams per 10,000 meters of a strand) of the elastic strands 86, and the tension imparted into the elastic strands 86 can all be varied to suit one's particular product needs. The elastic strands 86 can have a round, semi-circular, square, rectangular, oval or some other cross-sectional configuration. The elastic strands 86 can overlap, intersect or crisscross at least one other elastic strand 86. The various ways of positioning, orienting or securing the elastic strands 86 to the two outer layers 82 and 84 are well known to those skilled in the art.

The number of elastic strands 86 can range from 1 to about 20. The exact number of elastic strands 86 that are present will depend on the width (w) of the waist band 72, the diameter of each elastic strand 86, the arrangement of the elastic strands 86 on the two outer layers 82 and 84, etc. Desirably, from about 2 to about 10 elastic strands 86 are present in the waist band 72. More desirably, from about 3 to about 8 elastic strands 86 are present in the waist band 72. Most desirably, from about 4 to about 6 elastic strands 86 are present in the waist band 72. In FIGS. 2 and 3, three elastic strands 86 are depicted in the waist band 72.

Referring again to FIGS. 1 and 2, the three-piece disposable absorbent article 10 also includes a pair of leg bands 88 and 90. The leg band 88 is secured to the interior surface 22 of the front panel 12 and the leg band 90 is secured to the interior surface 36 of the back panel 26. Each of the pair of leg bands 88 and 90 is positioned adjacent to one of the second ends 16 and 30 of the front and back panels 12 and 26 respectively, and approximate leg openings 92 and 94, see FIG. 1.

Still referring to FIGS. 1 and 2, the absorbent assembly 48 is capable of being folded transversely, approximate the transverse central axis Y-Y. This folding enables the front panel 12 to overlap the back panel 26. When the absorbent assembly 48 is folded, the first and second side edges, 18 and 20 respectively, of the front panel 12 will align with the first and second side edges, 32 and 34 respectively, of the back panel 26. In addition, the first and second side edges, 78 and 80 respectively, of the waist band 72 will be aligned with the first and second side edges 18 and 20 of the front panel 12. After being folded, a pair of side seams 96 and 98 are formed which join the front panel 12 to the back panel 26 to create a closed unitary article, see FIG. 1. By "a closed unitary article" it is meant that the article, upon removal from its packaging, will appear similar to cloth underwear. A close unitary article is not similar to an infant diaper that has an open configuration and must be fastened to itself once it is positioned around a baby's torso.

The pair of side seams 96 and 98 form a secure bond that is normally unbreakable during use of the three-piece disposable absorbent article 10. However, the pair of side seams 96 ands 98 can be easily broken by the user or by a caregiver when the three-piece disposable absorbent article 10 is to be removed from the user's torso. By breaking the pair of side seams 96 and 98, the three-piece disposable absorbent article 10 can be quickly removed from the user's body and be discarded. Desirably, the pair of side seams 96 and 98 will form a bond that is not easily broken or opened during use but will be easily broken for removal. The pair of side seams 96 and 98 can be made using ultrasonics, heat, pressure, heat and pressure, adhesive, glue, or a combination of any of the aforementioned. In addition, the pair of side seams 96 and 98 can be formed by a chemical bond or by a mechanical bond, such as by sewing with a thread. These and other types of bonds are well known to those skilled in the art. Desirably, the pair of side seams 96 and 98 is formed using ultrasonic equipment.

Returning to FIG. 1, once the pair of side seams 96 and 98 is formed, the three-piece disposable absorbent article 10 acquires a pant-like appearance. The pant-like appearance will be very similar to cloth underwear. The three-piece disposable absorbent article 10 will have a waist opening 100 formed adjacent to the first ends 14 and 28 of the front and back panels, 12 and 26 respectively. The waist opening 100 is spaced apart from the pair of leg openings 92 and 94. Since the front and back panels, 12 and 26 respectively, are formed from an elastic material, the waist opening 100 and the pair of leg openings 92 and 94 can stretch and retract to accommodate the anatomy of the user and movement of the user's body.

Figure 4:
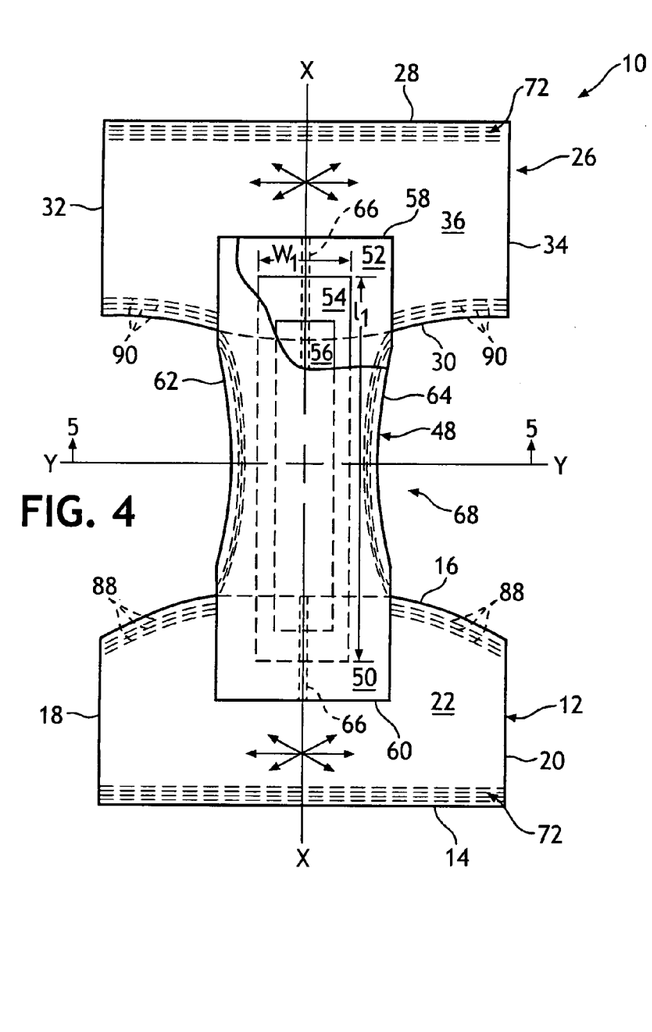
FIG. 4 is a plane view of the three-piece disposable absorbent article shown in FIG. 1 but depicted in an open position and marked by vectors showing the directions of stretch and retraction of the front, back and crotch panels and showing a partial cut away view of the absorbent assembly.

Referring now to FIG. 4, the three-piece disposable absorbent article 10 is shown with a partial cut away view exposing the absorbent assembly 48. In this view, one can clearly see that the absorbent 54 has a length $l_1$ and a width $w_1$. The length $l_1$ is aligned parallel to the longitudinal central axis X-X and the width $w_1$ is aligned parallel to the transverse central axis Y-Y.

Figure 5:
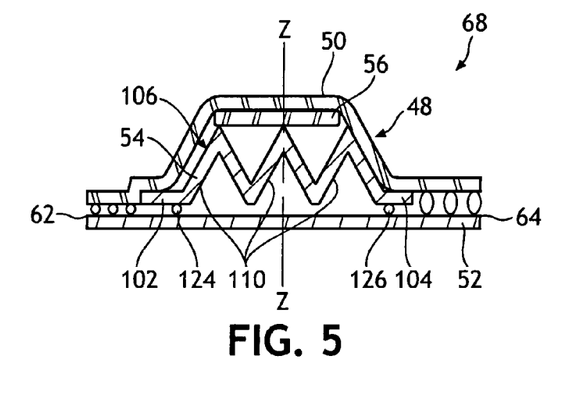
FIG. 5 is a cross-section view of the three-piece disposable absorbent article shown in FIG. 4 taken along line 5-5.
Figure 6:
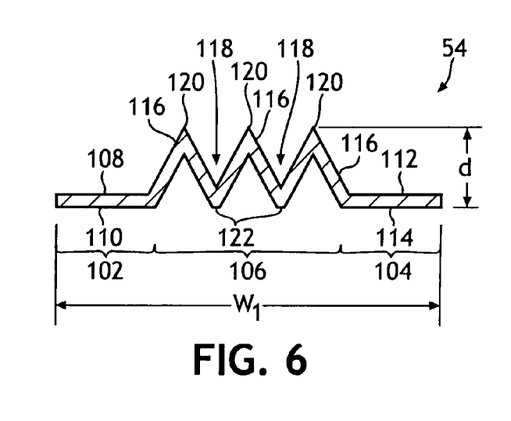
FIG. 6 is an enlarged view of the absorbent shown in FIG. 5.

Referring now to FIGS. 5 and 6, the absorbent 54 includes a pair of planar regions 102 and 104 separated by a non-planar region 106 extending across its width $w_1$. In other words, the non-planar region 106 is located in between the two planar regions 102 and 104. In FIG. 6, the planar region 102 is shown having an upper surface 108 and a lower surface 110 and the planar region 104 is shown having an upper surface 112 and a lower surface 114. The non-planar region 106 includes a plurality of alternating ridges 116 and valleys 118. The ridges and valleys, 116 and 118 respectively, can also be characterized as folds, pleats, bellows, undulations, creases, wrinkles, corrugations, rugosities or one or more z-folds. Each ridge 116 has a peak 120 and each valley 118 has a bottom point 122. Each of the peaks 120 extends above the upper surfaces 108 and 112 of the two planar regions, 102 and 104 respectively. In addition, each of the bottom points 122 is aligned parallel with the lower surfaces 110 and 114 of the two planar regions, 102 and 104 respectively. Alternatively, each of the bottom points 122 can be aligned below the lower surfaces 110 and 114 of the two planar regions, 102 and 104 respectively, if desired.

Still referring to FIG. 6, the vertical distance d located between a peak 120 and an adjacent bottom point 122 should be less than about 1 inch (about 25.4 mm). Desirably, the vertical distance d located between a peak 120 and an adjacent bottom point 122 should be less than about 0.75 inches (about 19 mm). More desirably, the vertical distance d located between a peak 120 and an adjacent bottom point 122 should be less than about 0.5 inches (about 12.7 mm).

The above described construction(s) are beneficial in keeping the non-planar region 106 close to the user's body. By so configuring the non-planar region 106, one can be assured that the non-planar region 106 is positioned to better receive body fluid and prevent fluid leakage from the three-piece disposable absorbent article 10.

Even when the non-planar region 106 is elongated, the peaks 120 of the ridges 116 will be aligned even with or be located above the upper surfaces 108 and 112 of the two planar regions, 102 and 104 respectively. Likewise, when the non-planar region 106 is elongated, the bottom points 122 of the valleys 118 will be evenly aligned with or be situated below the lower surfaces 110 and 114 of the two planar regions 102 and 104.

Referring again to FIG. 5, the three-piece disposable absorbent article 10 further includes a second attachment member 124 spaced apart from a third attachment member 126. The second attachment member 124 is located between the planar region 102 and the backsheet 52 just to the left of the non-planar region 106. The third attachment member 126 is located between the planar region 104 and the backsheet 52 just to the right of the non-planar region 106. The second and third attachment members, 124 and 126 respectively, can be adhesive, multiple adhesive bonds or one or more lines of adhesive. The line(s) of adhesive can be continuous or intermittent. When one or more lines of adhesive are used, they should be aligned parallel to the longitudinal central axis X-X. The lines of adhesive can extend along the length $l_1$ of the absorbent 54 or along a portion of the length $l_1$ of the absorbent 54. Desirably, the second and third attachment members, 124 and 126 respectively, can extend along at least about 50% of the length $l_1$ of the absorbent 54. More desirably, the second and third attachment members, 124 and 126 respectively, will extend along at least about 75% of the length $l_1$ of the absorbent 54. Even more desirably, the second and third attachment members, 124 and 126 respectively, can extend along from between about 75% to 100% of the length $l_1$ of the absorbent 54.

The second and third attachment members, 124 and 126 respectively, function to retain the non-planar region 106 in its initial configuration until the elastic backsheet 52 is stretched parallel to the direction of the transverse central axis Y-Y. When the elastic backsheet 52 is stretched to an extended state along the transverse central axis Y-Y, the second and third attachment members, 124 and 126 respectively, will be drawn further apart. This action will cause the non-planar region 106 to flatten to or towards a planar configuration. As this happens, the alternating ridges 116 and valleys 118 will acquire a flattened configuration. It should be noted that the non-elastic absorbent 54 can be elongated and contracted in only one direction when the elastic backsheet 52 is stretched and retracted, and that direction is aligned parallel to the transverse central axis Y-Y.

When the force used to stretch the elastic backsheet 52 is removed, the backsheet will retract to or towards its original dimension. As this occurs, the second and third attachment members, 124 and 126 respectively, will move closer together and cause the non-planar region 106 to again acquire a non-planar configuration.

While the invention has been described in conjunction with several specific embodiments, it is to be understood that many alternatives, modifications and variations will be apparent to those skilled in the art in light of the aforegoing description. Accordingly, this invention is intended to embrace all such alternatives, modifications and variations that fall within the spirit and scope of the appended claims.

I claim:

1. A three-piece disposable absorbent article having a longitudinal central axis and
a transverse central axis, comprising:
   a) a front panel capable of being stretched and retracted in multiple directions;
   b) a back panel capable of being stretched and retracted in multiple directions, said back panel being distinct and spaced apart from said front panel; and
   c) an absorbent assembly situated between said front and back panels and being attached to each by a first attachment member, said first attachment member being aligned along said longitudinal central axis, and said absorbent assembly including a non-elastic absorbent that is capable of being elongated and contracted in only one direction, that direction being aligned approximately parallel to said transverse central axis.

2. The three-piece disposable absorbent article of claim 1 wherein said absorbent assembly includes a liquid permeable bodyside liner and a liquid-impermeable backsheet which cooperate to enclose said non-elastic absorbent therebetween, and said bodyside liner and said backsheet are capable of being stretched and retracted in a direction parallel to said transverse central axis.

3. The three-piece disposable absorbent article of claim 2 wherein said bodyside liner and said backsheet are capable of being stretched and retracted in multiple directions.

4. The three-piece disposable absorbent article of claim 1 wherein said non-elastic absorbent has a length and a width, said length being aligned parallel to said longitudinal central axis and said width being aligned parallel to said transverse central axis, said width including a pair of planar regions separated by a non-planar region, and said non-planar region extending along said longitudinal central axis.

5. The three-piece disposable absorbent article of claim 4 wherein said non-planar region includes a plurality of alternating ridges and valleys.

6. The three-piece disposable absorbent article of claim 5 wherein each of said planar regions has an upper surface and a lower surface and each of said ridges has a peak that extends above said upper surfaces of each of said planar regions and each of said valleys has a bottom point that is evenly aligned with said lower surfaces of each of said planar regions.

7. The three-piece disposable absorbent article of claim 1 wherein said front and back panels are formed from an elastic material.

8. A three-piece disposable absorbent article having a longitudinal central axis and a transverse central axis, comprising:
   a) an elastic front panel capable of being stretched and retracted in multiple directions;
   b) an elastic back panel capable of being stretched and retracted in multiple directions, said back panel being distinct and spaced apart from said front panel; and
   c) an absorbent assembly situated between said front and back panels and being attached to each by a first attachment member, said first attachment member being aligned along said longitudinal central axis, said absorbent assembly including a liquid permeable bodyside liner, a liquid-impermeable backsheet and a non-elastic absorbent positioned therebetween, said bodyside liner and said backsheet being secured together to completely enclose said non-elastic absorbent, and said non-elastic absorbent is capable of being elongated and contracted in only one direction when said backsheet is stretched and retracted, and that direction is aligned approximately parallel to said transverse central axis.

9. The three-piece disposable absorbent article of claim 8 wherein said bodyside liner and said backsheet are capable of being stretched and retracted in multiple directions.

10. The three-piece disposable absorbent article of claim 8 wherein said non-elastic absorbent has a length and a width, said length being aligned parallel to said longitudinal central axis and said width being aligned parallel to said transverse central axis, said width including a pair of planar regions separated by a non-planar region, and said non-planar region extending along said longitudinal central axis.

11. The three-piece disposable absorbent article of claim 10 wherein said non-planar region includes a plurality of alternating ridges and valleys.

12. The three-piece disposable absorbent article of claim 11 wherein each of said planar regions has an upper surface and a lower surface and each of said ridges has a peak that extends above said upper surfaces of each of said planar regions and each of said valleys has a bottom point that is evenly aligned with said lower surfaces of each of said planar regions.

13. The three-piece disposable absorbent article of claim 11 wherein each of said planar regions has an upper surface and a lower surface and each of said ridges has a peak that extends above said upper surfaces of each of said planar regions and each of said valleys has a bottom point that is aligned below said lower surfaces of each of said planar regions.

* * * * *